United States Patent [19]
Basnight

[11] Patent Number: 5,222,945
[45] Date of Patent: Jun. 29, 1993

[54] HYPODERMIC SYRINGE WITH PROTECTIVE SHIELD

[76] Inventor: Robert W. Basnight, 5132 Linksland Dr., Holly Springs, N.C. 27540

[21] Appl. No.: 959,344

[22] Filed: Oct. 13, 1992

[51] Int. Cl.⁵ ............................................. A61M 5/00
[52] U.S. Cl. .................................. 604/110; 604/198; 604/218
[58] Field of Search ............... 604/198, 195, 192, 187, 604/110, 263, 218, 220

[56] References Cited

U.S. PATENT DOCUMENTS

| | | | |
|---|---|---|---|
| 4,801,295 | 1/1989 | Spencer | 604/198 |
| 4,813,940 | 3/1989 | Parry | 604/263 X |
| 4,820,272 | 4/1989 | Palmer | 604/220 X |
| 4,826,491 | 5/1989 | Schramm | 604/263 X |
| 4,994,045 | 2/1991 | Ranford | 604/198 |
| 5,024,660 | 6/1991 | McNaughton | 604/110 |
| 5,057,079 | 10/1991 | Tiemann et al. | 604/198 X |
| 5,104,385 | 4/1992 | Huband | 604/198 |
| 5,147,326 | 9/1992 | Talonn et al. | 604/110 X |

FOREIGN PATENT DOCUMENTS

89/00057 1/1989 World Int. Prop. O. .......... 604/110

*Primary Examiner*—John D. Yasko
*Attorney, Agent, or Firm*—Rhodes, Coats & Bennett

[57] ABSTRACT

A safety syringe includes a barrel having an interior chamber for containing a fluid, and a needle mounted at one end of the barrel. The needle has a bore in fluid communication with the interior chamber in the barrel. A plunger is slidably mounted within the interior chamber of the barrel for displacing fluid within the barrel through the needle to administer fluid to a patient. A protective shield is slidably mounted on the barrel and is moveable between an extended position in which the needle is concealed and a retracted position in which the needle is exposed. The protective shield is moveable between first, second, and third positions. In the first position, the protective shield is extended over the needle and is releasibly locked to protect the needle prior to use. In the second position, the protective shield is retracted and is releasibly locked to facilitate use of the syringe. In the third position, the protective shield is again extended to cover the needle and is irreversibly locked to prevent reuse of the syringe. Reuse of the syringe is further prevented by a plunger locking mechanism which is engaged when the plunger is fully depressed.

22 Claims, 4 Drawing Sheets

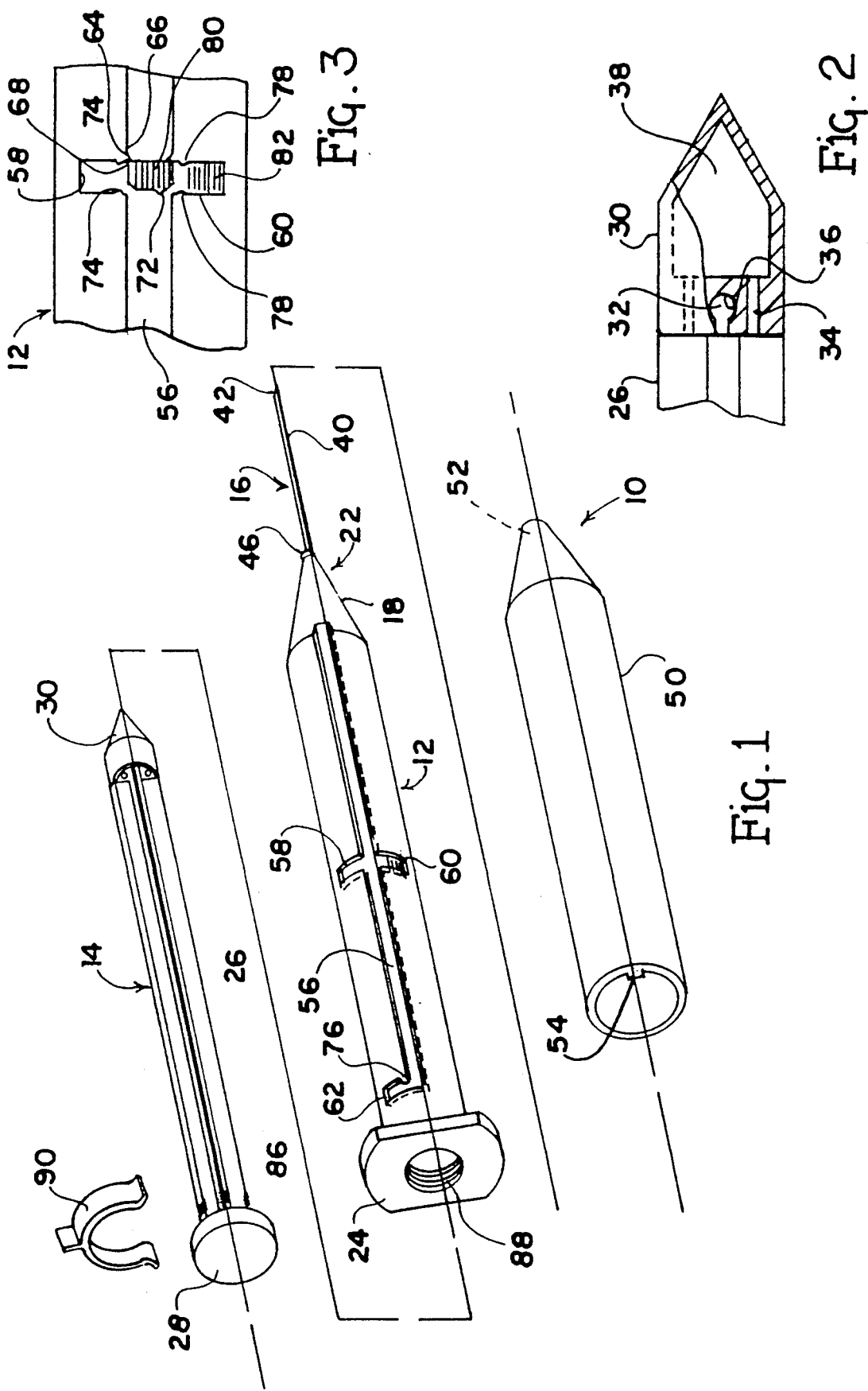

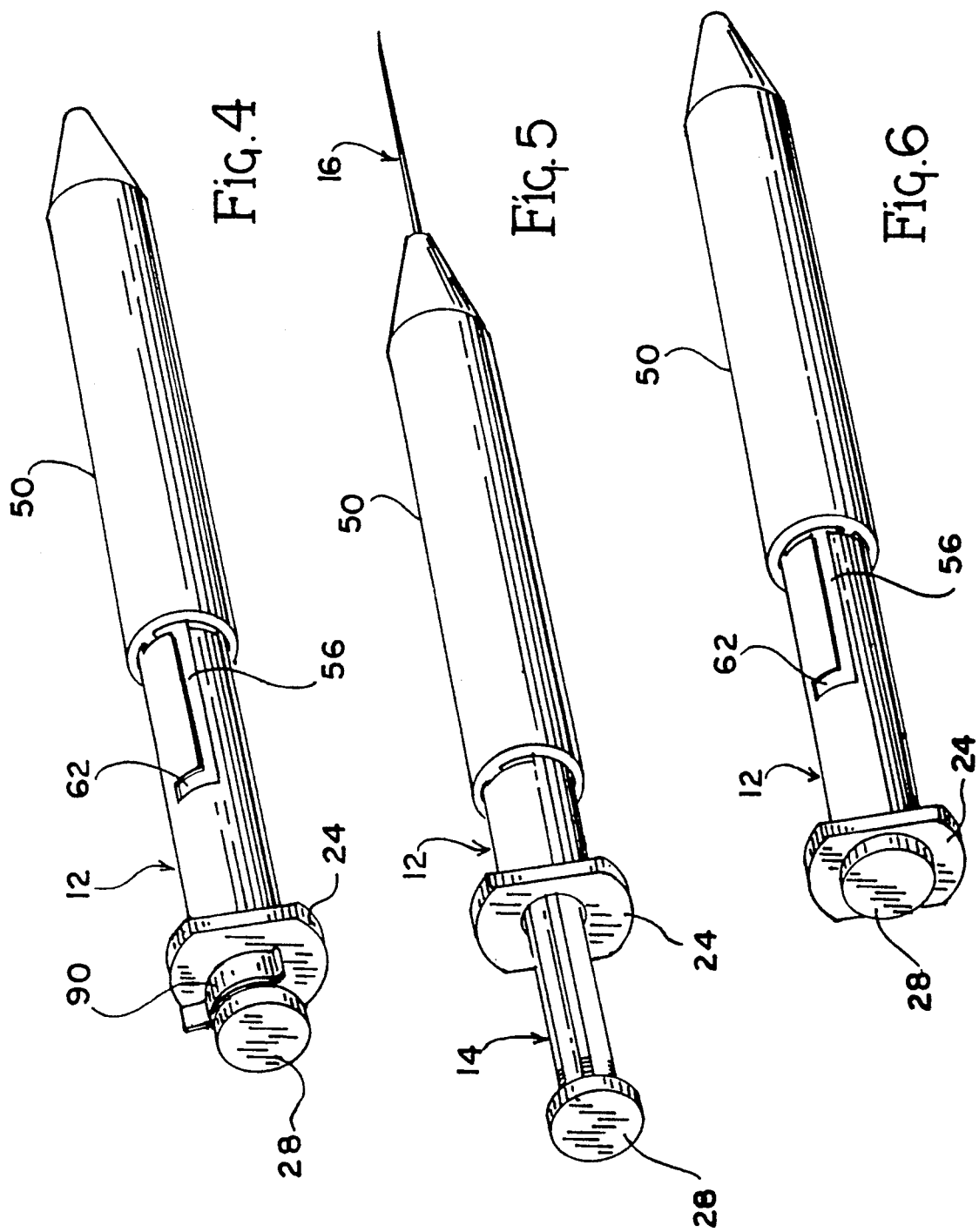

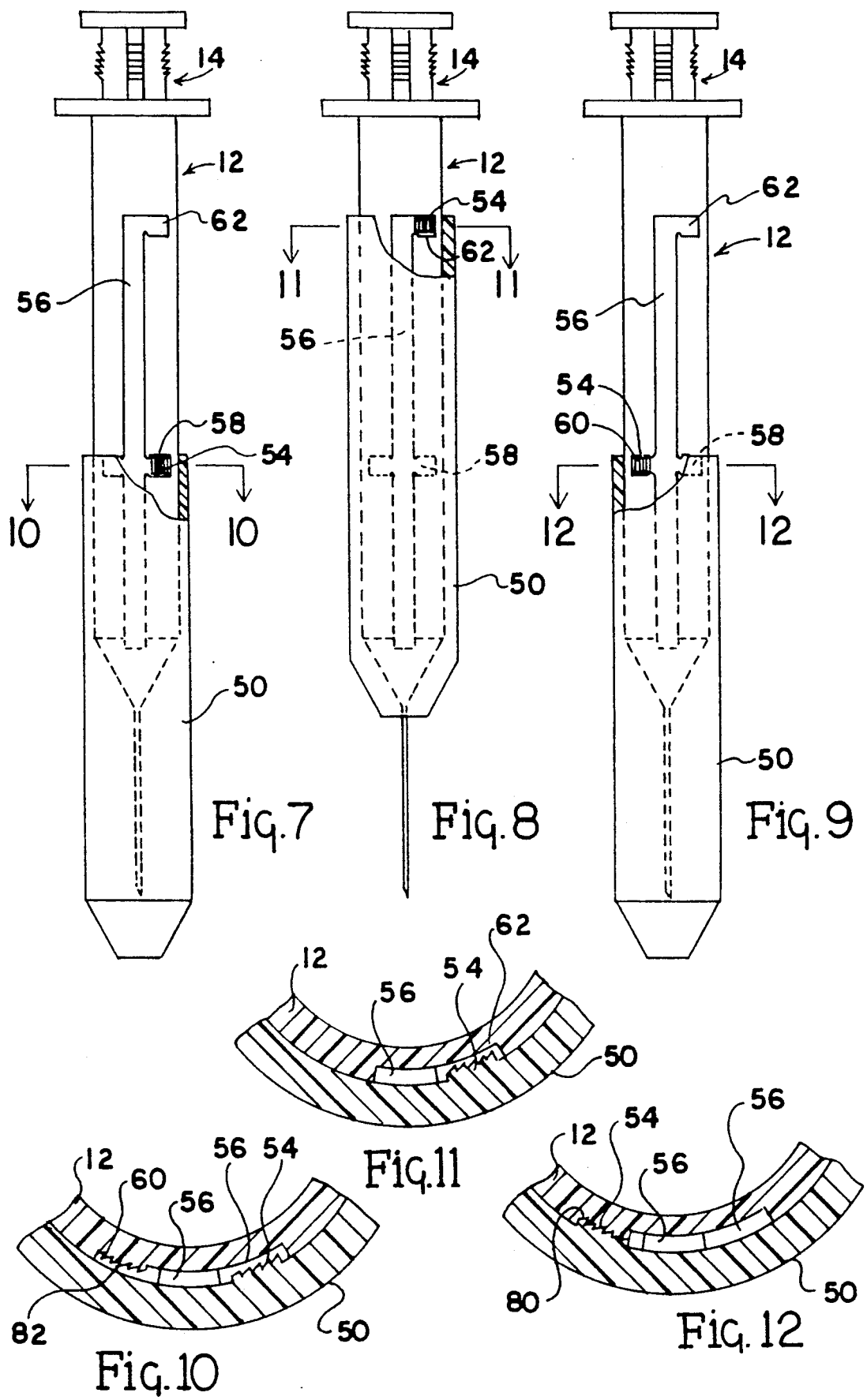

HYPODERMIC SYRINGE WITH PROTECTIVE SHIELD

BACKGROUND OF THE INVENTION

The present invention relates to hypodermic syringes and, in particular, to a safety syringe to prevent accidental needle pricks and reuse of a hypodermic syringe.

Syringes are often used for administering medication to patients suffering from infectious diseases. Numerous cases have been reported in which doctors, nurses, or other medical personnel have been infected by accidental needle pricks. The seriousness of the problem has become more acute in light of the recent spread of Acquired Immunodeficiency Syndrome (AIDS). Accordingly, it is of utmost importance that extreme care be exercised in the handling and disposal of hypodermic syringes after use to prevent the accidental transmission of the HIV virus, as well as other infectious diseases.

The spread of the HIV virus has often been attributed to the sharing of contaminated needles by illicit drug addicts. While most hypodermic needles are intended to be disposable, they are frequently reused and shared. Often times, the drug users obtain hypodermic syringes by stealing used syringes from hospitals and other medical facilities. Such needles may already be contaminated with the HIV virus. However, even when "clean" needles are obtained, it may still be infected with the HIV virus by one drug user and then transmitted to another drug user with whom the needle is shared.

In view of the seriousness of the AIDS epidemic, there is a need for a safety syringe which will help prevent accidental needle pricks and discourage illegal drug users from reusing or sharing needles. In the past, various types of guards or shielding devices have been devised for hypodermic needles to prevent accidental needle pricks. Typically, the guard is slidably mounted on the syringe barrel and is moveable from an extended position in which the protective shield overlies the needle and a retracted position in which the shield is retracted to expose the needle. These guards may include a latching mechanism for securing the guard in a particular position with respect to the needle and syringe. Patents which disclose an axially slidable shield or guard include U.S. Pat. Nos. 4,127,910 to Tallon et al; 5,120,309 to Watts; 4,801,295 to Spencer; and 3,890,971 to Leeson et al.

These prior art protective shields are generally suitable for protecting medical personnel from accidental needle pricks. These known devices satisfy many of the functional requirements of a protective shield. However, these prior art devices suffer from several drawbacks. One drawback is the complexity of the shield mechanism. Many of the prior art shields have complicated structures with multiple parts. The complexity of these devices makes them relatively costly to produce.

Another disadvantage with prior art safety syringes is that they do not effectively prevent reuse of a contaminated needle. Most of the prior art devices do not include an irreversible locking mechanism to secure the protective shield after use. As a result, it is possible to inadvertently reuse a needle which may have been contaminated. Even those protective devices which have irreversible locking mechanisms on the protective shield can be easily defeated by persons wanting to acquire such needles for illegal use. In most instances, the protective shield can be removed without destroying the function of the hypodermic syringe.

SUMMARY AND OBJECTS OF THE INVENTION

The present invention is a hypodermic syringe having a protective shield to prevent accidental needle pricks, and redundant locking mechanisms to prevent reuse of the syringe. The hypodermic syringe includes a barrel having a needle assembly mounted at one end thereof, and a plunger disposed within the barrel. The protective shield is slidably mounted on the barrel and is movable between an extended position in which the needle assembly is concealed, and a retracted position in which the needle assembly is exposed. The protective shield has three locking positions. The first locking position is used during storage and shipment of the syringe. In the first locking position, the protective shield is releasably locked in an extended position covering the needle. In the second position, the protective shield is moved to a retracted position to expose the needle. The protective shield is releasably locked in the second position to prevent the protective shield from interfering with the administration of medication to a patient. In the third locking position, the protective shield is again extended to conceal the needle. However, in the third locking position, the protective shield is irreversibly locked so that the syringe cannot be reused without destroying the protective shield.

In accordance with another aspect of the invention, a locking mechanism is provided for locking the plunger after the syringe has been used. The locking mechanism includes a first locking portion formed on the plunger and a second locking portion formed on the inner surface of the barrel. The first and second locking portions are engaged when the plunger is depressed. A collapsible piston is provided at the end of the plunger to facilitate engagement of the first and second locking portions. The plunger locking mechanism provides redundant protection against reuse of the syringe.

It is a primary object of the present invention to provide a syringe having a protective shield to protect the needle before and after use, and to prevent accidental needle pricks involving a used needle.

It is another object of the present invention to provide a hypodermic syringe having a protective shield which can be permanently and irreversibly locked after use so as to prevent reuse of the syringe either unintentionally or deliberately.

Another object of the present invention is to provide a hypodermic syringe having a locking mechanism for irreversibly locking the plunger to prevent reuse of the syringe either unintentionally or deliberately.

Still another object of the present invention is to provide a safety syringe which is relatively simple in construction, economical to manufacture, and easy to use.

Other objects and advantages of the present invention will become apparent and obvious from a study of the following description and the accompanying drawings which are merely illustrative of such invention.

BRIEF DESCRIPTION OF THE DRAWINGS

FIG. 1 is an exploded perspective of the hypodermic syringe of the present invention.

FIG. 2 is a detailed elevation illustrating the tip of the plunger.

FIG. 3 is a detailed elevation showing a portion of the barrel of the syringe.

FIG. 4 is a perspective view of the syringe showing the protective shield in the first position.

FIG. 5 is a perspective view of the syringe showing the protective shield in the second position.

FIG. 6 is a perspective view of the syringe showing the protective shield in the third position.

FIG. 7 is an elevation view of the syringe showing the protective shield in the first position.

FIG. 8 is an elevation view of the hypodermic syringe showing the protective shield in the second position.

FIG. 9 is an elevation view of the hypodermic syringe showing the protective shield in a third, irreversibly locked position.

FIG. 10 is a cross-sectional view of the hypodermic syringe taken through line 10—10 of FIG. 7.

FIG. 11 is a cross-sectional view of the hypodermic syringe taken through line 11—11 of FIG. 8.

FIG. 12 is a cross-sectional view of the hypodermic syringe taken through line 12—12 of FIG. 9.

DETAILED DESCRIPTION OF THE INVENTION

Figures 13, 14:
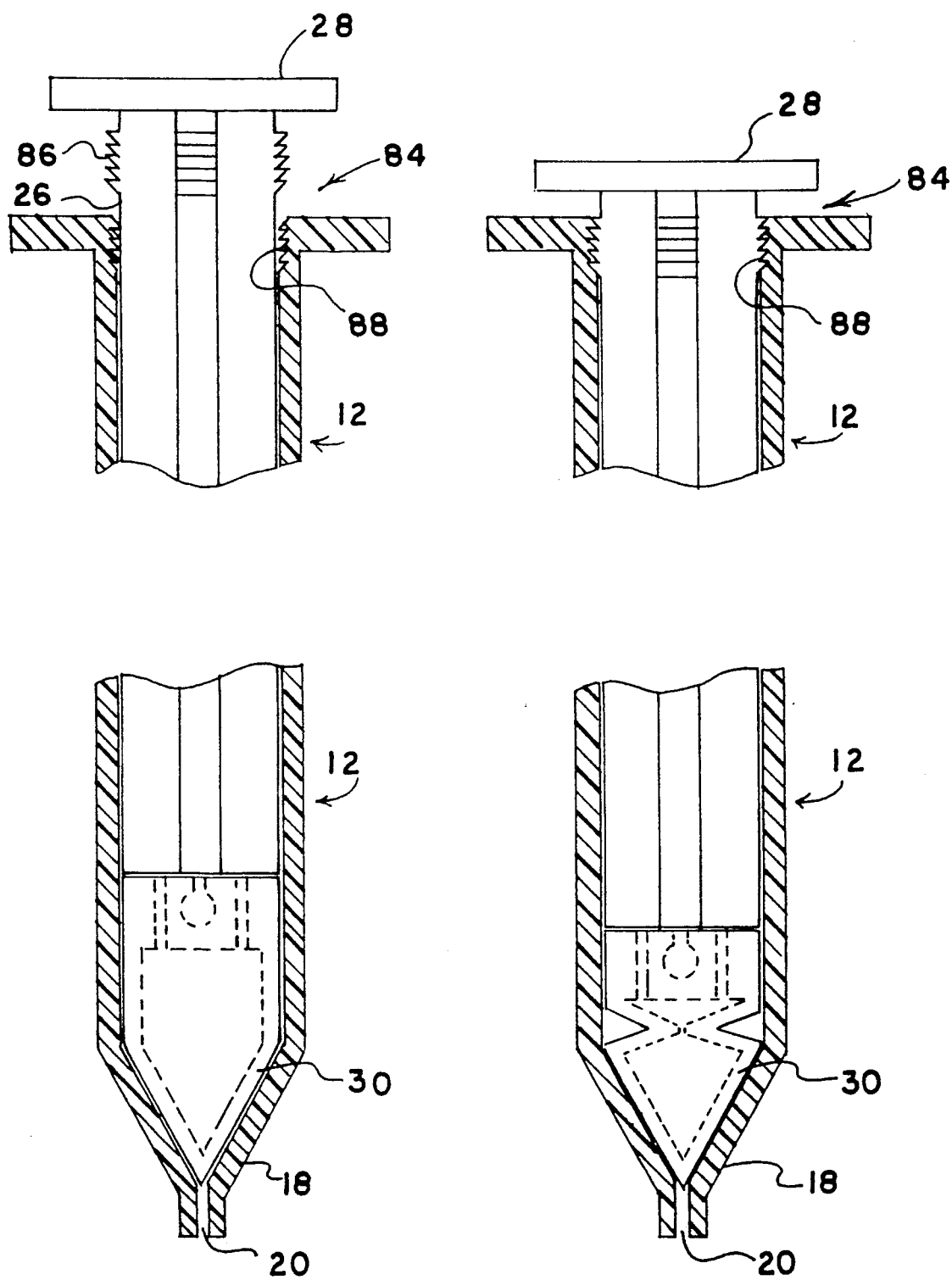
FIG. 13 is a fragmented-section view of the hypodermic syringe showing the plunger in an unlocked position.
FIG. 14 is a fragmented-section view of the hypodermic syringe showing the plunger in a locked position.

Referring now to the drawings, and particularly to FIGS. 1-6, a preferred embodiment of the hypodermic syringe of the present invention is disclosed and indicated generally by the numeral 10. The hypodermic syringe includes a generally cylindrical barrel 12, a plunger 14 slidably mounted within the barrel 12, and a needle assembly 16 mounted on the distal end of the barrel 12 through which the contents of the barrel 12 are dispensed when the plunger 14 is depressed. The end of the barrel 12 on which the needle assembly 16 is mounted has a conical configuration and includes an aperture 20 which communicates with the needle bore (not shown). Surrounding the aperture 20 is a first half of a locking mechanism 22, such as a leur lock, for securing the needle assembly 16 to the barrel 12. Locking mechanisms of this type are well-known to those skilled in the art.

The end of the barrel 12 opposite the conical tip 18 is open to receive the plunger 14. A finger flange 24 projects radially outwardly from the barrel 12. The finger flange 24 is adapted to be engaged by the index finger and middle finger during administration of medication as will be hereinafter described in greater detail.

The plunger 14 includes an elongated shaft 26 having a thumb pad 28 at one end and a rubber piston 30 at the opposite end. The piston 30 is slidable in the barrel 12, but in sealing relation with respect to the inner surface of the barrel so that when the plunger 14 is moved forwardly, the contents of the barrel 12 are displaced through the needle assembly 16. The piston 30 is held in place by a rounded projection 32 which fits into a correspondingly shaped opening 36 in the bottom of the piston 30. The piston 30 has a conical configuration to conform to the conical tip 18 of the barrel 12, and has a hollow interior 38. The piston 30 should be made of a material having sufficient rigidity to resist collapsing during administration of medication until the piston 30 seats against the conical tip 18 of the barrel 12. After the piston 30 is seated against the end of the barrel 12, any further pressure exerted by the user will cause the piston 30 to collapse. The air holes 34 in the bottom of the piston 30 facilitate the collapsing of the piston 30 by allowing air within the hollow interior 38 of the piston 30 to escape.

The needle assembly 16 includes an elongated hollow shaft having a sharp point 42 at one end thereof. An internal lumen (not shown) extends through the needle shaft 40 and terminates in an aperture (not shown) near the point 42. Opposite the needle's point is a connecting hub (not shown) which includes a second portion of the locking mechanism designed to cooperate with and securely lock to the first portion of the locking mechanism on the barrel 12. As previously mentioned, the conventional locking mechanism used for this application is a leur lock. The needle assembly 16 is positioned such that the internal lumen communicates with the aperture 20 in the barrel 12 such that the contents of the barrel 12 pass through the needle assembly 16 when the plunger 14 is depressed.

To protect the sharp tip 42 of the needle 16 after it has been used, the syringe 10 of the present invention includes a protective shield 50. The protective shield 50 is slidably mounted on the barrel 12 and is movable between first, second, and third positions. In the first position, the protective shield 50 is extended to cover the needle assembly 16. The protective shield 50 is yieldably locked in this position during shipping and storage of the syringe 10 prior to use. When it is desired to use the syringe 10, the shield 50 is moved to a second position in which the needle assembly 16 is exposed. With the protective shield 50 in the second position, the syringe 10 can be used to administer the medication to a patient. After the needle is used, the protective shield 50 is moved to a third position in which the protective shield 50 is again extended to cover the needle assembly 16. In this third position, however, the protective shield 50 is irreversibly locked. Consequently, in this "disposal state", the syringe 10 cannot be accidentally reused, and the needle assembly 16 is covered to prevent accidental needle pricks.

To achieve the above-described functions, the barrel 12 of the syringe 10 is provided with a pair of longitudinally extending guide channels 56 on opposite sides of the barrel 12 which extend parallel to the longitudinal axis of the barrel 10. The guide channels 56 are formed in the outer surface of the barrel 12 and are approximately 0.01 inches deep. On the inner surface of the protective shield there are a pair of keys 54 which fit into the guide channels 56 and guide the protective shield 50 as it is moved between its extended and retracted positions.

A pair of locking channels 58 and 60 intersect each guide channel 56 approximately midway between the conical tip 18 and the finger flange 24. A third locking channel 62 intersects each guide channel 56 at the proximal end of the guide channel 56. The purpose of the locking channels 58, 60 and 62 is to lock the protective shield 50 in the first, second, and third positions respectively.

To facilitate assembly of the protective shield 50 onto the barrel 12 of the syringe 10, each guide channel 56 extends to the conical tip 18 of the barrel 12. The protective shield 50 is mounted onto the barrel 12 by aligning the keys 54 on the protective shield 50 with the guide channels 56 on the barrel 12 and then sliding the shield 50 axially onto the barrel 12. To prevent the protective shield 50 from being removed, the guide channels 56 are formed with a pair of stops 64 which are positioned immediately adjacent to the locking channels 58 and 60. The stops 64 include a ramp or camming surface 66 and a back wall 68 which is contiguous with one side wall of the locking channels 58 and 60. The keys 54 are provided with a pair of camming surfaces 70 having a slope which permits the key 54 to ride over the ramps 66 in one direction only. After passing over the stops 64, the key 54 is prevented from moving beyond the locking channels 58 and 60. The stops 64 not only prevent removal of the protective shield 50 from the barrel 12 of the syringe 10, but also facilitate the alignment of the key 54 with the locking channels 58 and 60 during use without requiring too much attention of the medical practitioner.

As previously indicated, the protective shield 50 can be locked in three distinct positions. In the first position, referred to herein as the storage position, the protective shield 50 is extended and rotated relative to the barrel 12 such that the key 54 is received in the locking channel 58. FIGS. 4, 7, and 10 illustrate the protective shield 50 in the "storage" position. To retain the protective shield 50 in the storage position, the key 54 is provided with a pair of detents 72 which ride over a matching pair of detents 74 in the side walls of the locking channel 58. The detents 72 and 74 require a deliberate application of rotational force to the protective shield 50 to rotate the key 54 into the locking channel 58.

In the second position, referred to as the "use" position, the key 54 on the protective shield 50 is received in the locking channel 62. FIGS. 5, 8, and 11 illustrate the protective shield 50 in the "use" position. The locking channel 62 is also provided with a pair of detents 76 which cooperate with the detents 72 on the key 54 to releasibly lock the protective shield 50 in a retracted position during use of the syringe 10. Thus, it is apparent that once the key 54 is engaged in the locking channels 58 or 62, the detents 72, 74, and 76 will prevent the protective shield from inadvertently slipping out of a respective locking channels 58 and 62.

In the third position, referred to as the "disposal" position, the protective shield 50 is again moved to an extended position and rotated such that the key 54 on the protective shield is received in the locking channel 60. FIGS. 6, 9, and 12 illustrate the protective shield 50 in the "disposal" position. A plurality of serrations 82 are formed in the bottom of the locking channel 60 which are engaged by corresponding serrations 80 on the top surface of the key 54. The configuration of the serrations 80 and 82 is such that the key 54 can move in only one direction—that is, into the locking channel 60. Once the serrations 80 and 82 are engaged with one another, the protective shield cannot be rotated to back the key 54 out of the locking channel 60. This irreversible locking mechanism prevents the syringe 10 from being reused. Thus, it is important to prevent the user from unintentionly placing the protective shield 50 in this position.

To prevent unintentional locking of the protective shield 50 in the disposal condition, a set of detents 78 are formed in the side walls of the locking channel 60. The detents 78 in the side walls of the locking channel 60 cooperate with the detents 72 on the key 54 to prevent the key 54 from being rotated into the locking channel 60 by mistake. It takes a deliberate application of rotational force to the protective shield 50 to rotate the key 54 into the locking channel 60. Once the key 54 is rotated into the locking channel 60, the protective shield 50 is irreversibly locked and the syringe is rendered inoperative since the needle is concealed.

It should be apparent that the protective shield of the present invention can be utilized with not only hypodermic syringes, but also other types of devices in the medical art which employ a needle. For example, the protective shield could be used on a standard IV needle or in a vacutainer.

The present invention also includes means for locking the plunger 14 after use of the syringe 10 to further prevent reuse of the syringe 10. Referring now to FIGS. 13 and 14, it is seen that the plunger 14 includes a locking mechanism indicated generally at 84 for locking the plunger after use. The plunger locking mechanism 84 comprises a plurality of serrations 86 formed on the shaft 26 on the plunger 14. Corresponding serrations 88 are formed on the inside of the barrel 12 adjacent to the finger flange 24. The length of the plunger shaft 26 should allow the piston 30 to sea against the conical tip 16 of the barrel 12 without the serrations 80 and 82 being engaged. This is necessary to allow medical personnel to properly draw fluid into the hypodermic syringe 10. After use, the plunger 14 is drawn back to draw fluid into the syringe 10. During administration of the medication to a patient, the plunger 14 is depressed to displace the contents of the syringe 10 through the needle assembly 16 and into the patient's blood stream. Once the piston 30 seats against the conical tip 18 of the barrel 12, any further pressure exerted on the plunger 14 will cause the piston 30 to collapse. As the piston 30 collapses, the serrations 86 on the shaft 26 of the plunger 14 engage the serrations 88 on the inner surface of the barrel 12, as can be most clearly seen in FIG. 14. The configuration of the serrations 86 and 88 prevents the plunger 14 from being pulled back out of the barrel 12.

A generally c-shaped clip 90 is placed on the shaft 26 of the plunger 14 during shipping and storage to cover the serrations 86 and to prevent the plunger 14 from being inadvertently locked prior to use. The clip 90 snaps onto the plunger 14 and functions as a spacer to prevent the plunger 14 from being accidently depressed thereby "locking" the plunger 14 and rendering the syringe 10 useless.

The syringe 10 will be initially positioned, as shown in FIGS. 4 and 7, and is usually contained in a sterile package. After removing the syringe 10 from the sterile package, the medical professional grasps the syringe 10 in the right hand, and holds the protective shield 50 with the left hand. The protective shield 50 is rotated to disengage the key 54 from the locking channel 58. Once the key 54 is aligned with the guide channel 56, the protective shield 50 is slid axially down in the barrel 12 until the key 54 engages the end of the guide channel 56. The protective shield 50 is then rotated to engage the key 54 in the locking channel 62, as shown in FIGS. 5, 8, and 11. In this position, the needle assembly 16 is exposed. The syringe 10 is typically filled with fluid by placing the needle 16 in a liquid container and pulling the plunger 14 back to draw the liquid into the syringe 10. The needle 16 is then inserted into the patient in the normal manner, and the plunger 14 is depressed by applying pressure to the thumb pad 28.

After administration of the medication, the plunger 14 is firmly pressed to collapse the piston 30, as shown in FIG. 14, to lock the plunger 14. The left hand is then used to grasp the protective shield 50 and to rotate the protective shield 50 so as to disengage the key 54 from the locking channel 62. The protective shield 50 is then slid axially along the barrel 12 to an extended position. When the key 54 engages the stops 64, the protective shield 50 is rotated into the locking channel 60. In this position, the needle assembly 16 is completely enclosed by the protective shield 50. Thus, there is no chance of any medical professional accidently wounding himself with the syringe. Further, the protective shield is irreversibly locked to prevent reuse of the syringe 10 absent deliberate destruction of the protective shield 50. Even if the protective shield 50 were destroyed by someone obtaining the syringe 10 for illegal drug use, the plunger 14 would still be irreversibly locked in the barrel 12.

It is apparent from the foregoing that the safety syringe 10 of the present invention is useful in preventing accidental needle pricks which is one of the major health hazards facing medical professionals. Further, the protective shield 50 of the syringe 10 can be irreversibly locked after use to prevent the syringe 10 from being reused by mistake. Further, a redundant locking mechanism is provided for the plunger 14 to prevent reuse of the needle, either deliberately or by mistake.

The present invention may, of course, be carried out in other specific ways than those herein set forth without departing from the spirit and essential characteristics of the invention. The present embodiments are, therefore, to be considered in all respects as illustrative and not restrictive and all changes coming within the meaning and equivalency range of the appended claims are intended to be embraced therein.

I claim:

1. A safety syringe comprising:
   (a) a barrel having an interior chamber for containing a fluid and at least one longitudinally extending guide channel;
   (b) a needle mounted to the barrel at one end of the barrel, said needle having a bore in fluid communication with the interior chamber in the barrel;
   (c) a plunger slidably mounted within the interior chamber of the barrel for displacing the fluid within the barrel through the needle to administer fluid to a patient;
   (d) a protective shield slidably mounted on the barrel and movable between an extended position in which the needle is concealed and a retracted position in which the needle is exposed;
   (e) a key secured to the protective shield which fits into the guide channel of the barrel to guide the movement of the protective shield between the extended and retracted positions, said key including a plurality of serrations;
   (f) means for releasably locking the protective shield in a first, extended position prior to the syringe being used;
   (g) means for releasably locking the protective shield in a second retracted position to facilitate use of the syringe; and
   (h) means for irreversibly locking the protective shield in a third extended position after the syringe has been used to prevent reuse of the syringe, said irreversible locking means including a plurality of serrations formed on the barrel of the syringe which are engageable with the serrations on the key of the protective shield to irreversibly lock the protective shield in the third position.

2. The safety syringe of claim 1 wherein the barrel of the syringe includes at least one longitudinally extending guide channels, and wherein the protective shield includes a key which fits into the guide channel on the barrel to guide the movement of the protective shield between the extended and retracted positions.

3. The safety syringe of claim 1 wherein the means for releasibly locking the protective shield in the first position comprises a first locking channel that intersects with the guide channel for receiving the key on the protective shield when the protective shield is in the first position, wherein the key is insertable into the first locking channel by rotating the protective shield relative to the barrel.

4. The safety syringe of claim 3 wherein the first locking channel includes detent means for releasably holding the key on the protective shield in the first locking channel.

5. The safety syringe of claim 1 wherein the means for releasibly locking the protective shield in the second position comprises a second locking channel that intersects with the guide channel for receiving the key on the protective shield when the protective shield is in the second position, wherein the key is insertable into the second locking channel by rotating the protective shield relative to the barrel.

6. The safety syringe of claim 5 wherein the second locking channel includes detent means for releasably holding the key on the protective shield in the second locking channel.

7. The safety syringe of claim 1 wherein the means for releasibly locking the protective shield in the third position comprises a third locking channel that intersects with the guide channel for receiving the key on the protective shield when the protective shield is in the third position, wherein the key is insertable into the third locking channel by rotating the protective shield relative to the barrel.

8. The safety syringe of claim 1 further including plunger locking means for irreversibly locking the plunger after use to prevent reuse of the syringe.

9. The safety syringe of claim 8 wherein the plunger locking means includes a first locking component formed on the plunger and a second locking component formed inside the barrel engageable with the first locking component on the plunger.

10. The safety syringe of claim 9 wherein the plunger includes a collapsible tip and wherein the first and second locking components are engageable with one another only when the tip of the plunger is collapsed by pressing the tip of the plunger against the end of the barrel.

11. The safety syringe of claim 10 wherein the first and second locking components comprise serrations formed respectively on the plunger and the barrel, and wherein the serrations are shaped to permit axial movement of the plunger relative to the barrel in a first direction, and to prevent axial movement of the plunger relative to the barrel in a second direction.

12. A safety syringe comprising:
   (a) a barrel comprising an interior chamber for containing a fluid;
   (b) a needle mounted to the barrel at one end of the barrel, the needle having a bore in a fluid communication with the interior chamber in the barrel;
   (c) a plunger slidably mounted within the interior chamber of the barrel for displacing the fluid within the barrel through the needle to administer fluid to a patient;
   (d) a protective shield slidably mounted on the barrel and moveable between an extended position in which the needle is concealed, and a retracted position in which the needle is exposed;

(e) guide means for guiding the protective shield as it is moved between the extended and retracted positions relative to the barrel, the guide means including a longitudinally extending guide channel formed on one of the two parts, and a key having a plurality of serrations formed in the other of the two parts, wherein the key on one of the two parts is slidable in the guide channel in the other of the two parts;

(f) a first locking channel which intersects with the guide channel for receiving the key when the protective shield is placed in a first position wherein the first locking channel includes means for releasibly holding the key within the first locking channel;

(g) a second locking channel which intersects the guide channel for receiving the key when the protective shield is in a second locking position, wherein the second locking channel includes means for releasably holding the key within the second locking channel; and (h) a third locking channel which intersects with the guide channel for receiving the key when the protective shield is in a third position, the third locking channel including serrations for engaging the serrations on the key to irreversibly retain the key within the third locking channel, and to prevent reuse of the syringe.

13. The safety syringe of claim 12 wherein the first locking channel includes detent means for releasibly holding the key in the first locking channel.

14. The safety syringe of claim 12 wherein the second locking channel includes detent means for releasibly holding the key in the second locking channel.

15. The safety syringe of claim 12 further including one-way stop means formed in the guide channel for retaining the protective shield on the barrel of the syringe.

16. The safety syringe of claim 15 wherein the stop means comprises a pair of ramps formed in the side walls of the guide channel, and a pair of camming surfaces formed on the key, wherein the ramps in the guide channel and the camming surfaces on the key cooperate to allow the key to pass over the ramps in one direction only.

17. A safety syringe comprising:
(a) a barrel having an interior chamber for containing a fluid;
(b) a needle mounted to the barrel at one end of the barrel, said needle having a bore in fluid communication with the interior chamber in the barrel;
(c) a plunger having a collapsible tip slidably mounted within the interior chamber of the barrel for displacing the fluid within the barrel through the needle to administer fluid to a patient; and
(d) plunger locking means for irreversibly locking the plunger when the collapsible tip is collapsed to prevent reuse of a syringe.

18. The safety syringe of claim 17 wherein the plunger locking means includes a first locking component formed on the plunger and a second locking component formed inside the barrel engageable with the first locking component on the plunger.

19. The safety syringe of claim 18 wherein the first and second locking components comprise serrations formed respectively on the plunger and the barrel, and wherein the serrations are shaped to permit axial movement of the plunger relative to the barrel in a first direction, and to prevent axial movement of the plunger relative to the barrel in a second direction.

20. The safety syringe of claim 18 further including spacer disposable around the shaft of the plunger to prevent accidental locking of the plunger.

21. The safety syringe of claim 20 wherein the spacer comprises a generally c-shaped clip.

22. A medical device comprising:
(a) a main body having an interior chamber for containing a fluid;
(b) a needle mounted to the main body and having a bore in fluid communication with the interior chamber in the main body;
(c) a protective shield slidably mounted on the main body and moveable between an extended position in which the needle is concealed and a retracted position in which the needle is exposed;
(d) guide means for guiding the protective shield as it is moved between the extended and retracted positions relative to the main body, the guide means including a longitudinally extending guide channel formed on one of the two parts, and a key having a plurality of serrations formed on the other of the two parts, wherein the key on one of the two parts is slidable in the guide channel in the other of the two parts;
(e) a first locking channel which intersects with the guide channel for receiving the key when the protective shield is placed in a first extended position, wherein the first locking channel includes a means for releasably holding the key within the first locking channel;
(f) a second locking channel which intersects the guide channel for receiving the key when the protective shield is in a second retracted locking position, wherein the second locking channel includes means for releasably holding the key within the second locking channel; and
(g) a third locking channel which intersects with the guide channel for receiving the key when the protective shield is in a third extended position, a third locking channel including serrations engageable with the serrations on the key to irreversibly retain the key within the third locking channel and to prevent reuse of the device.

* * * * *